United States Patent
Soluri et al.

(10) Patent No.: US 12,085,681 B2
(45) Date of Patent: Sep. 10, 2024

(54) DIRECTIONAL GAMMA DETECTOR

(71) Applicant: CONSIGLIO NAZIONALE DELLE RICERCHE, Rome (IT)

(72) Inventors: Alessandro Soluri, Rome (IT); Roberto Massari, Nettuno (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 92 days.

(21) Appl. No.: 17/919,241

(22) PCT Filed: Mar. 24, 2021

(86) PCT No.: PCT/IB2021/052428
§ 371 (c)(1),
(2) Date: Oct. 14, 2022

(87) PCT Pub. No.: WO2021/209842
PCT Pub. Date: Oct. 21, 2021

(65) Prior Publication Data
US 2023/0161056 A1 May 25, 2023

(30) Foreign Application Priority Data
Apr. 15, 2020 (IT) ......................... 102020000007978

(51) Int. Cl.
*G01T 1/202* (2006.01)
*A61B 6/00* (2006.01)
(Continued)

(52) U.S. Cl.
CPC ............ *G01T 1/202* (2013.01); *A61B 6/4258* (2013.01); *A61B 6/4266* (2013.01);
(Continued)

(58) Field of Classification Search
CPC ... G01T 1/202; G01T 1/1612; G01T 1/20184; G01T 1/161; G01T 7/00; G01T 1/166;
(Continued)

(56) References Cited

U.S. PATENT DOCUMENTS 5,070,878 A * 12/1991 Denen .................. A61B 6/4258
250/336.1
5,151,598 A *  9/1992 Denen .................. H03F 3/1935
600/431
(Continued)

FOREIGN PATENT DOCUMENTS

| WO | 01/22866    | 4/2001  |
| WO | 2012/171009 | 12/2012 |
| WO | 2019/090441 | 5/2019  |

OTHER PUBLICATIONS

International Search Report dated Jun. 30, 2021, for PCT/IB2021/052428, 4 pp.
(Continued)

*Primary Examiner* — Kiho Kim
(74) *Attorney, Agent, or Firm* — NIXON & VANDERHYE

(57) ABSTRACT

Described is a directional gamma detector including a detection probe and a handgrip, wherein the detection probe includes: a supporting rod and a detection head coupled or integrated with a first end of the supporting rod. The detection head includes a plurality of detection elements distinct from each other for simultaneously detecting gamma rays directed in different directions and including at least one scintillation crystal and a corresponding first electronic conversion circuitry. Each detection element is associated with a respective collimator. The handgrip is equipped internally with a second electronic circuitry for converting the signals. The detection probe, and in particular a second end of the supporting rod, is reversibly connectable to the (Continued)

handgrip by a mechanical connector equipped with electrical contacts for transferring the signals from the first electronic conversion circuitry to the second electronic conversion circuitry.

19 Claims, 6 Drawing Sheets

(51) Int. Cl.
    *A61B 6/42*         (2024.01)
    *G01T 1/161*      (2006.01)
    *G01T 1/20*       (2006.01)
    *A61B 6/12*       (2006.01)

(52) U.S. Cl.
    CPC .......... *A61B 6/4411* (2013.01); *G01T 1/1612* (2013.01); *G01T 1/20184* (2020.05); *A61B 6/12* (2013.01)

(58) Field of Classification Search
    CPC ... A61B 6/4258; A61B 6/4266; A61B 6/4411; A61B 6/12; A61B 6/461
    See application file for complete search history.

(56) References Cited

U.S. PATENT DOCUMENTS

| | | |
|---|---|---|
| 5,916,167 A | 6/1999 | Kramer et al. |
| 2004/0204646 A1 | 10/2004 | Nagler et al. |
| 2013/0338490 A1 | 12/2013 | Wendler |
| 2014/0249402 A1 | 9/2014 | Kimchy et al. |
| 2018/0235556 A1* | 8/2018 | Speeg .................... G01T 1/202 |

OTHER PUBLICATIONS

Written Opinion of the ISA dated Jun. 30, 2021, for PCT/IB2021/052428, 7 pp.

* cited by examiner

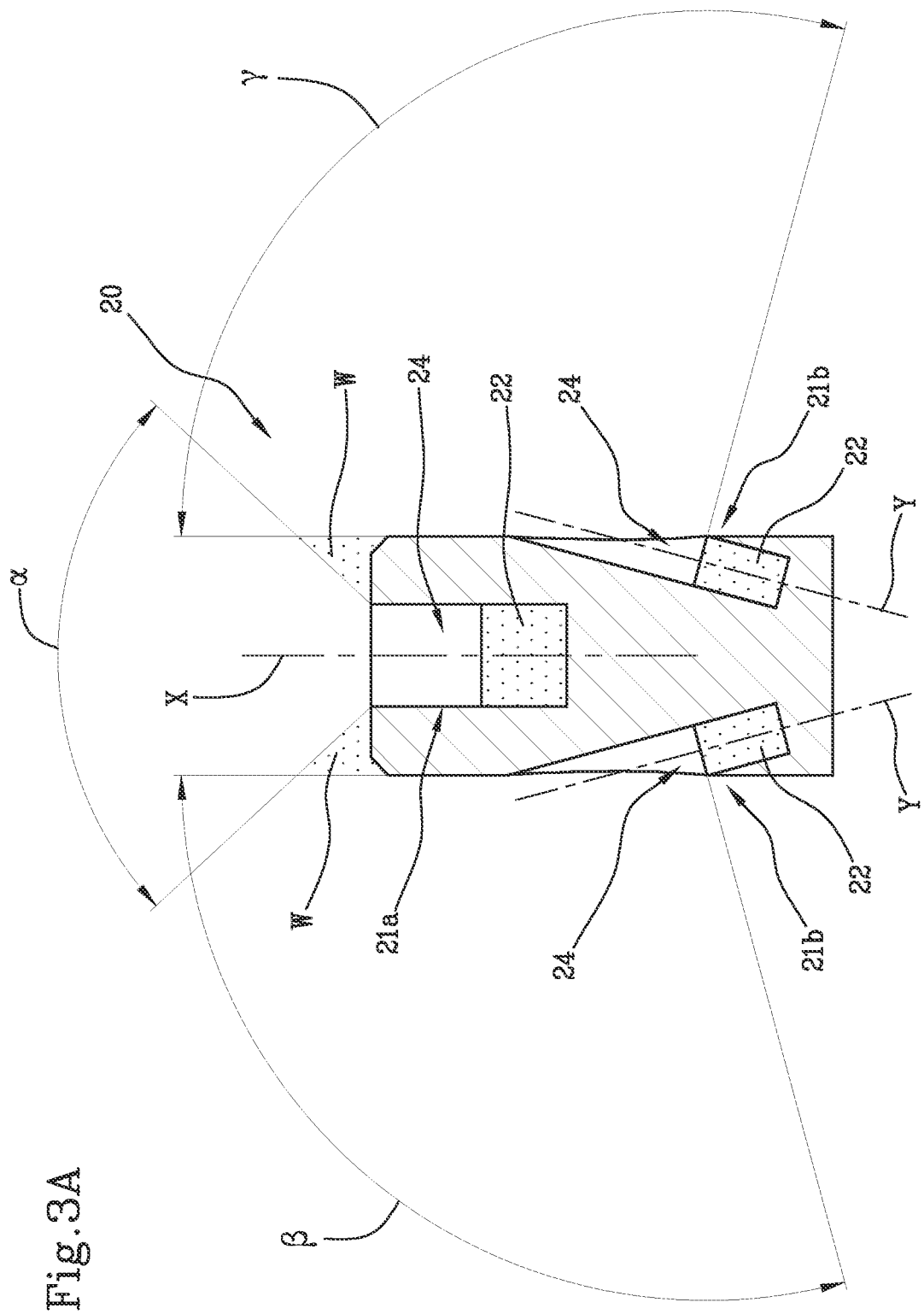

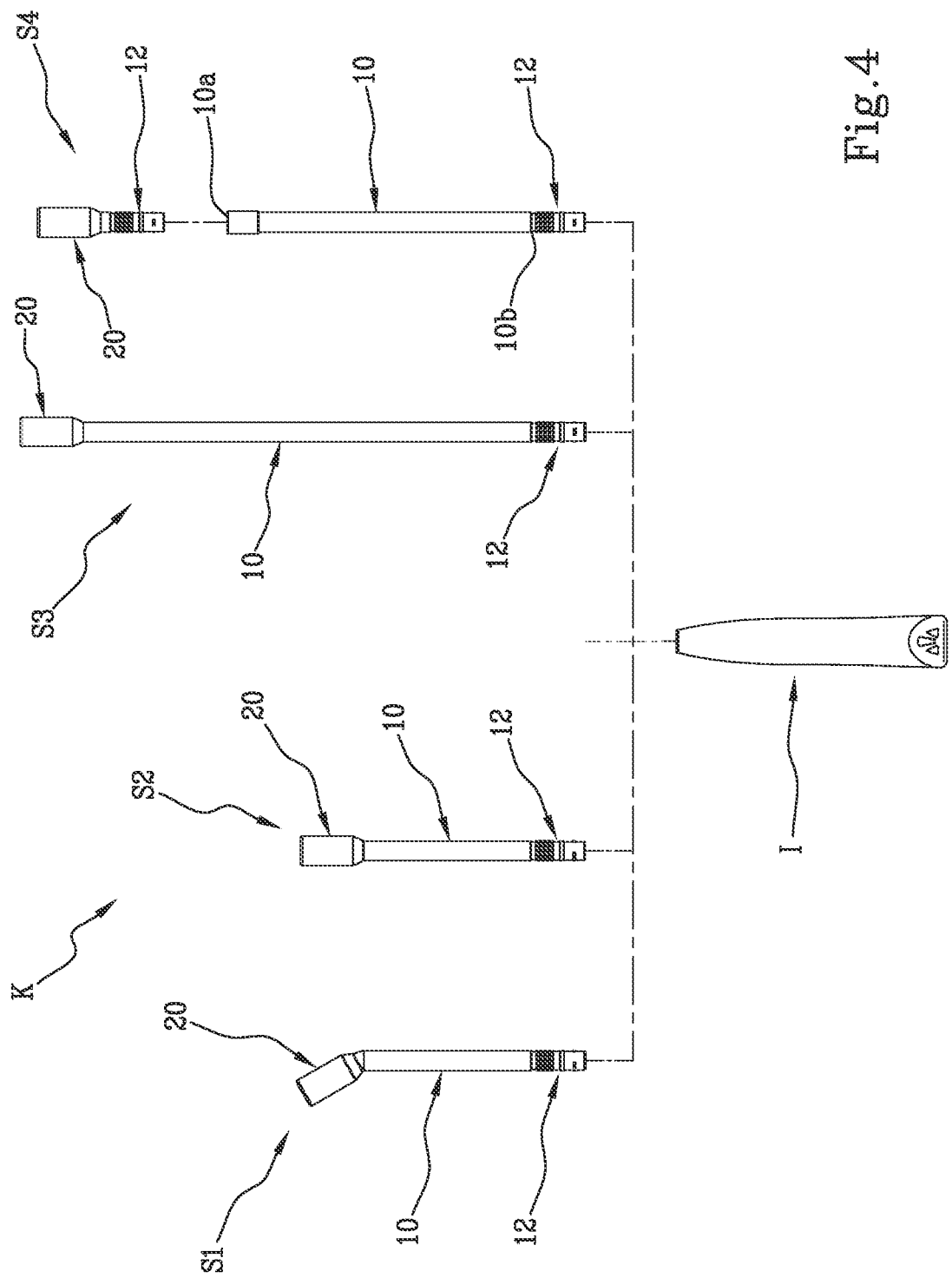

DIRECTIONAL GAMMA DETECTOR

CROSS-REFERENCE TO RELATED APPLICATION(S)

This application is the U.S. national phase of International Application No. PCT/IB2021/052428 filed Mar. 24, 2021 which designated the U.S. and claims priority to IT 102020000007978 filed Apr. 15, 2020, the entire contents of each of which are hereby incorporated by reference.

BACKGROUND OF THE INVENTION

Field of the Invention

This invention relates to a directional gamma detector which can be widely applied in the field of radio-guided surgery (intraoperative and laparoscopic) for locating lymph nodes and tumors and/or other diseases.

Description of the Related Art

As is known, gamma detectors are instruments used to locate tumor cells or specific diseased parts in a patient by picking up the radiation emitted by a radiopharmaceutical previously administered to the patient and which tends to concentrate in the diseased cells.

Generally speaking, gamma detectors comprise a detection head equipped with a single crystal or a plurality of crystals suitably oriented and configured to absorb the gamma rays emitted by the radiopharmaceutical. The prior art scintigraphic detection devices also comprise a rod configured to receive at one end the detection head and at a further end a handgrip configured for suitably directing the detection head during the medical application. In the prior art gamma detection devices, the handgrip usually contains all the control electronics configured for converting the data coming from the detection head and for transmitting it to a processing system in such a way as to be subsequently displayed by an operator.

In more detail, there are currently prior art detectors with a large range of action also known as "goniometric detectors" comprising a first detection element which is hollow and tubular in shape and which is divided into at least three sectors, each consisting of a scintillation crystal, and a second detection element consisting of a scintillation crystal housed inside the tubular structure of the first detection element.

In other words, the detectors with a large range of action have a detection head divided into a central part, configured to impart an axial directionality, and a series of angular sectors which are able to indicate the directionality of the radiation. The directionality of the radiation is obtained by making the above-mentioned crystals using materials having different optical properties.

As is known, the detectors with a large range, thanks to this arrangement of the crystals, can analyze zones not facing directly the front surface of the detector, allowing the identification of lymph nodes and tumors even delocalized with respect to the front portion of the instrument. The detectors with a large range are not, however, provided with structures for collimation of the gamma rays incident on the crystals and they therefore have a low spatial resolution to identify the tumor or more generically the part of the patient affected by the disease.

Gamma probes are also known which are equipped with a detection head made of a material with a high atomic number and having a plurality of detection elements, each comprising a scintillation crystal. These crystals are distinct from each other and aligned according to respective different collimation axes for simultaneously detecting gamma radiation directed in different directions. Each detection element is associated with a collimator made of a material with a high atomic number and designed to block the gamma rays incident upon the detection element at a predetermined external solid angle. Usually, these detectors have an axial collimator and at least two lateral collimators, inclined relative to the axial collimator in such a way that the central crystal acts as a true and proper detector whilst the lateral crystals act as direction sensors to indicate to the operator where to direct the instrument during the medical analysis.

Disadvantageously, the above-mentioned types of scintigraphic detectors have drawbacks linked in particular to their precision and their cost.

The detectors with a large range of action, as they are free of collimators, have low spatial resolutions which make these detectors not very reliable and not very precise. Moreover, these detection devices are large in size due to the tubular configuration of the crystals which do not adapt well to the miniaturization characteristics required by the current detection instruments.

One disadvantage of the detectors with a head made of a material with a high atomic number is that the dimensions of the detection head crystals are equivalent to each other but, since they have a different orientation within the detection head itself, they have different solid angles of view.

In other words, even though the scintillator crystals have the same size, they are able to absorb gamma rays according to different angles of view since they are positioned on the detection head at different angles from each other. More specifically, the lateral scintillator crystals have a visible angle greater than that of the scintillator crystal positioned coaxially to the detector. This results in an analysis which basically favors the detection of the lateral crystals which have a greater angular opening but for this reduced collimation, thus obtaining an imprecise detection.

A further disadvantage derives from the fact that the lateral crystals, which are inclined relative to the central crystal, due to the respective collimator, have detection angles which are insufficient in size to carry out an angular detection over a large area, thus adversely affecting the detection speed which requires a greater skill of the operator or implies a greater number of maneuvers carried out by the operator to determine the correct position of the central crystal aligned with the source of emission.

In other words, only the rays whose angle is within the size of the angle of view delimited by a crystal are actually detected; all the other rays, on the other hand, fall in a blind zone in which they are not detected. Since the solid angles described by prior art scintillator crystals do not intersect each other, certain rays will have directions such as to fall into the space between two solid angles and will not therefore be analyzed, thus reducing the detection speed.

More generally speaking, prior art detectors do not have geometries and arrangements of the detection elements which are favorable to a precise and rapid analysis of the part of the patient affected by the disease.

A further disadvantage derives from the fact that both of the detection configurations described above have a poor operational flexibility, since their application is limited to the specific use and, in the case of different uses, it is necessary to provide additional instruments with a considerable increase in costs. Consider, for example, investigations using rectilinear probes, investigations which require the use of angular detection heads or laparoscopic investigations. In these situations, the operator must have different probes each designed for the respective use, with obvious increases in costs. In fact, it is known that the greatest incidence of cost in these probes is the complex electronic control circuitry configured for converting the data coming from the detection head and for transmitting it to the processing system.

SUMMARY OF THE INVENTION

The technical purpose of the invention is therefore to provide a directional gamma detector which is able to overcome the drawbacks of the prior art.

The aim of the invention is to provide a directional gamma detector which is extremely precise and reliable.

A further aim of the invention is to provide a directional gamma detector having a limited cost.

A further aim of the invention is to provide a directional gamma detector which is extremely versatile in use.

A further aim of the invention is to provide a directional gamma detector having a particular production geometry which is able to speed up the localization of the tumor or, more generally, of the lesion.

The technical purpose indicated and the aims specified are substantially achieved by a directional gamma detector comprising the technical features described in one or more of the appended claims. More specifically, the technical purpose is achieved by a directional gamma detector comprising a detection probe and a handgrip, where the detection probe comprises a supporting rod and a detection head coupled or integrated with a first end (distal) of the supporting rod and a plurality of detection elements distinct from each other for simultaneously detecting gamma rays directed in different directions to each other. Each detection element comprises at least one scintillation crystal and a corresponding first electronic conversion circuitry to receive an optical signal from the crystal and convert it into an electrical signal, each of the detection elements is associated with a respective collimator made of a material with a high atomic number and suitable for screening the gamma rays incident upon the detection element with a predetermined external angle and a solid angle, the handgrip can be manually gripped by an operator and is equipped internally with a second electronic circuitry for converting the signals.

The detector according to the invention is characterized in that detection probe, and in particular a second end (proximal) of the supporting rod, is reversibly connectable to the handgrip by means of a mechanical connector equipped with electrical contacts for transferring the signals from the first electronic conversion circuitry to the second electronic conversion circuitry.

Preferably, the mechanical connector is a bayonet coupling, a quick coupling, a snap-on coupling or a threaded connection or threaded ring nut.

Preferably, the handgrip has a transversal dimension greater than that of the supporting rod and even more preferably between the handgrip and the supporting rod there is a variation of transversal cross-section on which the mechanical connector is positioned.

Advantageously, thanks to the mechanical connector, the handgrip is a shared component applicable to each detection probe, quickly and easily, as a function of the specific use necessary each time.

Advantageously, the costs relative to the detector are considerably reduced since a single handgrip is necessary (which is usually the most costly part of the entire detector since it contains the majority of the operating electronics) to operate with different detection probes.

Further features and advantages of the invention are more apparent in the non-limiting description which follows of a non-exclusive embodiment of a directional gamma detector.

BRIEF DESCRIPTION OF THE DRAWINGS

The description is set out below with reference to the accompanying drawings which are provided solely for purposes of illustration without restricting the scope of the invention and in which:

FIGS. 3A and 3B show respective embodiments of a cross-section according to a longitudinal plane of the portion of the directional gamma detector of FIG. 2;

FIG. 4 shows a front view of a kit for configuring a directional gamma detector according to the invention.

DESCRIPTION OF THE PREFERRED EMBODIMENTS

With reference to the accompanying drawings, the "R" denotes a directional gamma detector according to the invention, according to a first embodiment.

Figure 1A:
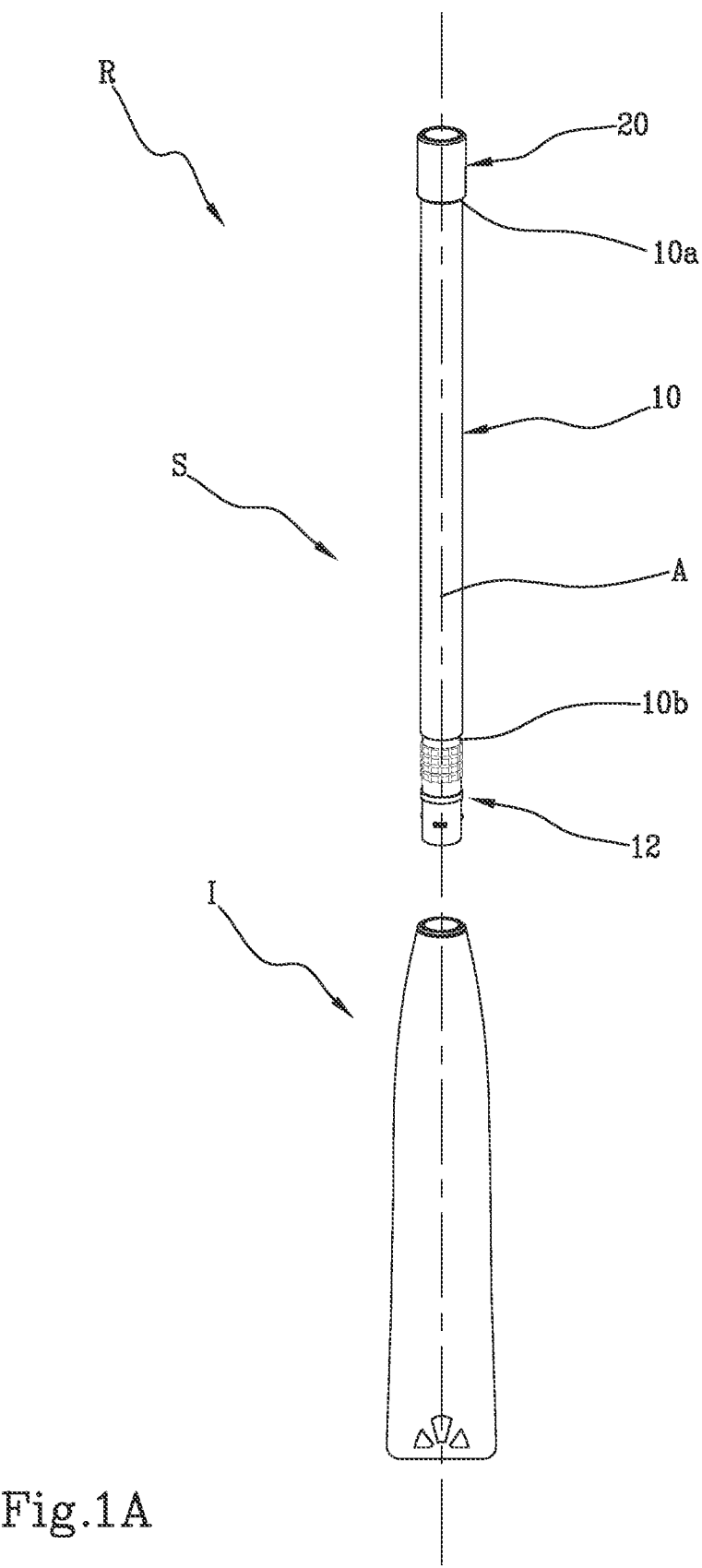
FIGS. 1A and 1B show, respectively, an exploded view and an operating configuration view of a directional gamma detector according to the invention.

As shown in FIG. 1A, the detector "R" comprises a detection probe "S" and a handgrip "I", aligned along a main axis of extension "A" of the detector "R".

The detection probe "S" comprises a supporting rod 10, extending along the main axis of extension "A" of the detector "R", and a detection head 20 coupled or integrated with a first end 10a of the supporting rod 10.

Figure 1B:
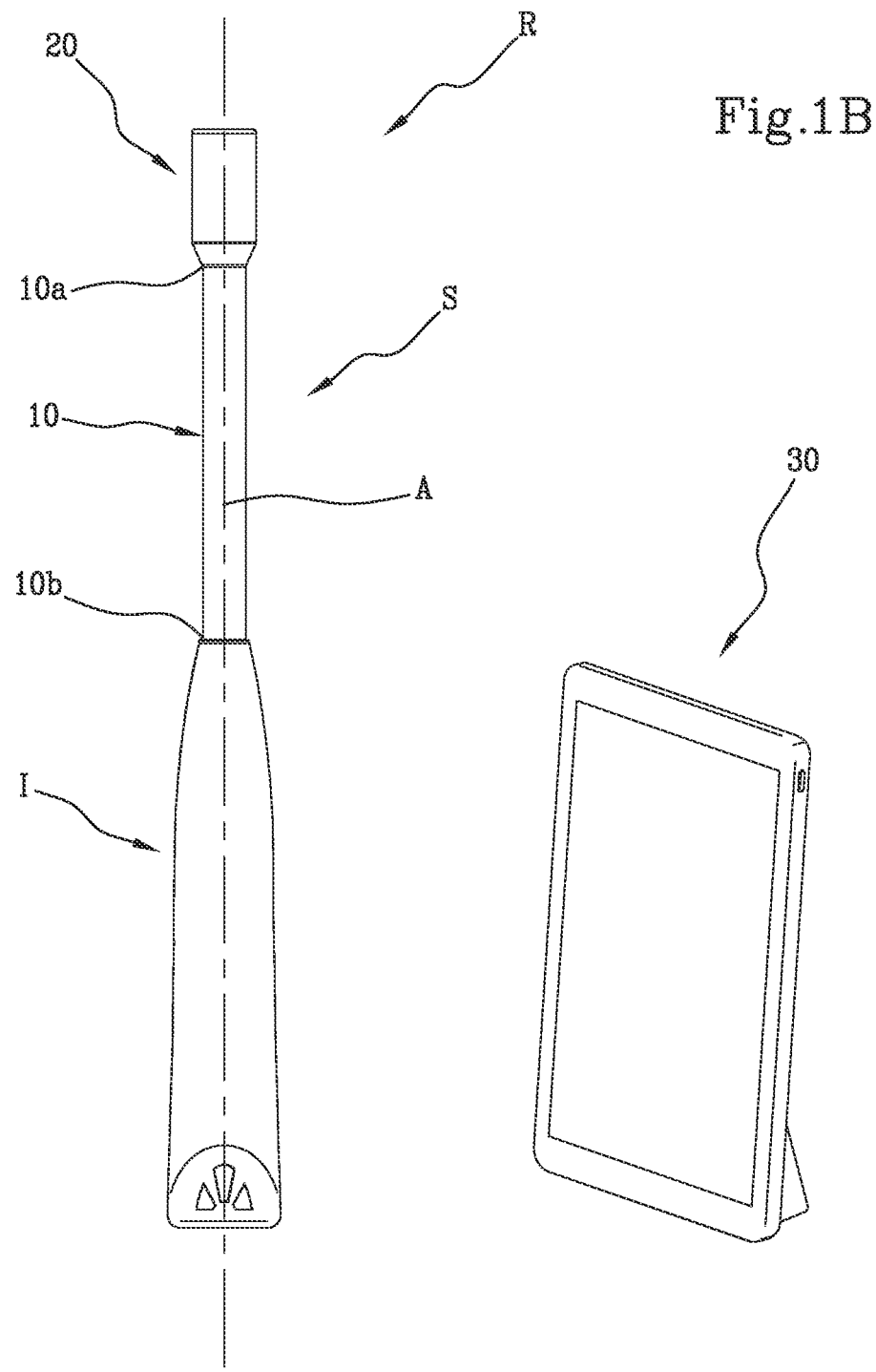

Advantageously, according to the invention, the handgrip "I" is reversibly connectable to the detection probe "S" by a mechanical connector 12, as described in detail below, in such a way as to obtain a detector "R" made of at least two functionally different components and which can be physically separated from each other as shown in FIG. 1B.

The detection probe "S" comprises a supporting rod 10 and a detection head 20 coupled or integrated with a first end 10a of the supporting rod 10.

Figure 2:
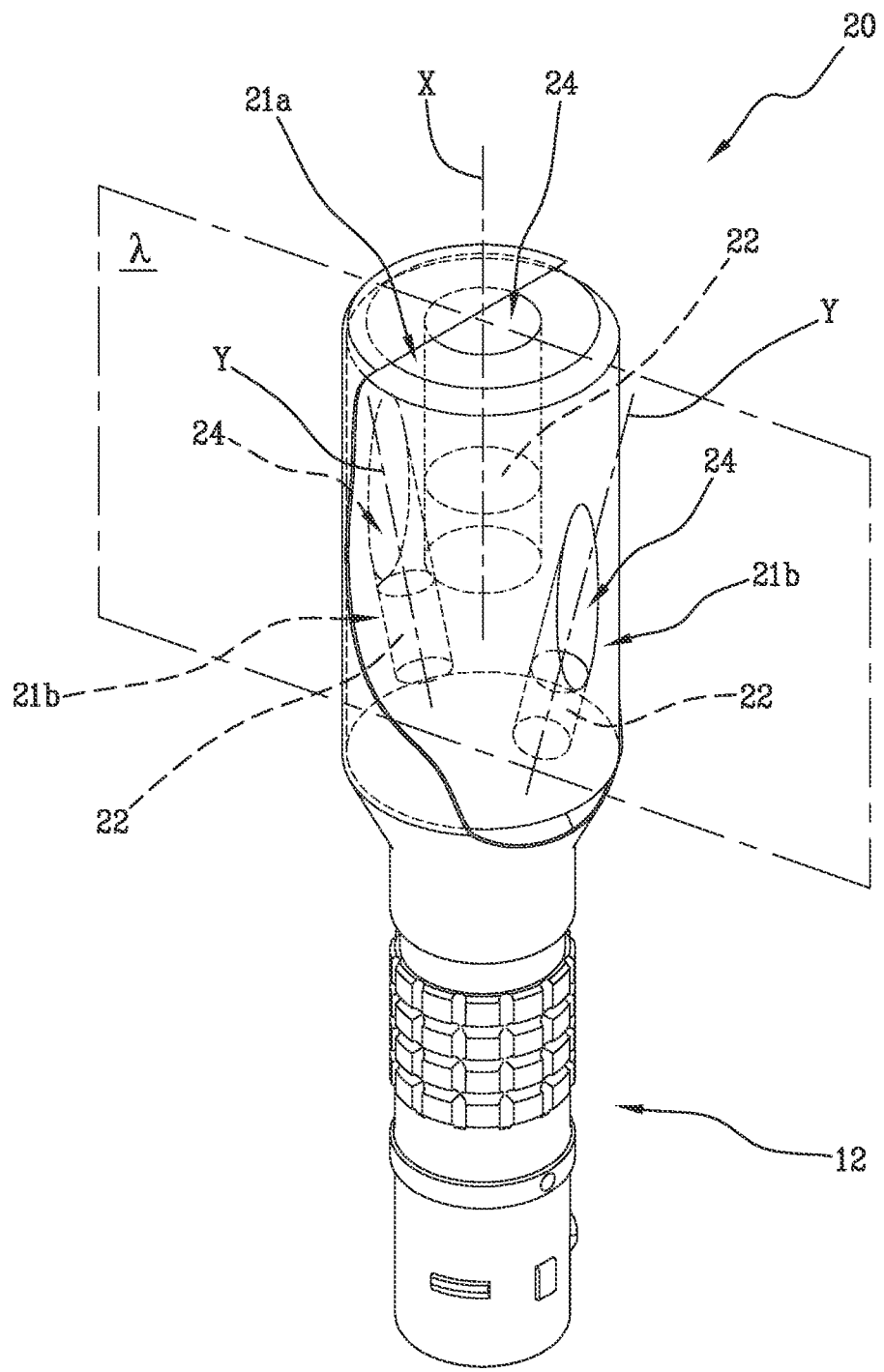
FIG. 2 shows a perspective view of a portion of the directional gamma detector according to the invention in an alternative embodiment.

According to the embodiment of FIG. 2, the supporting head 20 is of the type removably connectable to the supporting rod 10 by means of a further mechanical connector 12 (for example of the same configuration and/or size as that defining the connection between the supporting rod 10 and the handgrip "I"). However, according to an alternative embodiment, the supporting head 20 is integrated with the supporting rod 10, that is to say, made as one piece.

As shown in detail in FIG. 2, the supporting head 20 is made in the form of a solid body having a cylindrical shape preferably extending along the main axis of extension "A". The term "solid body" is used to mean a block made of a single material. In the preferred embodiment, the detection head 20 is made of a material with a high atomic number, for example lead, designed to absorb and screen the gamma rays emitted by a radiopharmaceutical.

The solid body comprises a plurality of detection elements 21a, 21b distinct from each other for simultaneously detecting gamma rays directed along respective directions different to each other. In the embodiment shown in the accompanying drawings, the detection head 20 comprises a central detection element 21a aligned with a main collimation axis "X", preferably parallel or coaxial with the main direction of extension "A" of the supporting rod 10, and a pair of lateral detection elements 21b aligned along respective collimation directions "Y" transversal to the main collimation axis "X" and preferably diverging away from the handgrip "I".

Preferably, the collimation directions "Y" transversal to the main axis of collimation "X" lie in a plane of symmetry "I" of the detection head 20 passing through the central collimation axis "X" (FIG. 2).

Even more preferably, the transversal collimation directions "Y" are inclined at an angle of between 20° and 90° relative to the main axis of collimation "X", this angle being measured in the above-mentioned plane of symmetry "I".

As shown in FIG. 2, the lateral detection elements 21b are opposite each other, diametrically opposite the central detection element 21a and lie at the same height on the detection head 20. In other words, the lateral detection elements 21b are positioned symmetrically about a longitudinal plane passing through the above-mentioned main direction of extension "A" of the supporting rod 10 and/or through the main axis of collimation "X".

Alternatively, the lateral detection elements 21b are opposite each other, diametrically opposite the central detection element 21a and lie at different heights on the detection head 20, that is to say, in such a way as to be axially offset.

Preferably, the lateral detection elements 21b are shaped and/or positioned in such a way that at least a part of the central detection element 21a, and in particular at least the rear part, is in a region of the detection head 20 positioned radially between the lateral detection elements 21b and/or between the respective channels in which the lateral detection elements 21b are positioned. In other words, the lateral detection elements 21b and/or the channels in which they are housed enclose laterally and at least partly the central detection element 21a, in particular at least the rear of the latter (in particular thanks to the divergent shape "forwards" of the axes "Y" of the lateral detection elements 21b. In this configuration, shown in FIGS. 3A to 3B, a particular compactness of the detection head 20 is obtained in an axial direction.

In another possible embodiment not illustrated, the detection head 20 comprises a single central detection element 21a and a plurality of lateral detection elements 21b aligned along respective collimation directions "Y" transversal to the main collimation axis "X" and angularly positioned at predetermined angular distances around the central detection element 21a.

Figure 3B:
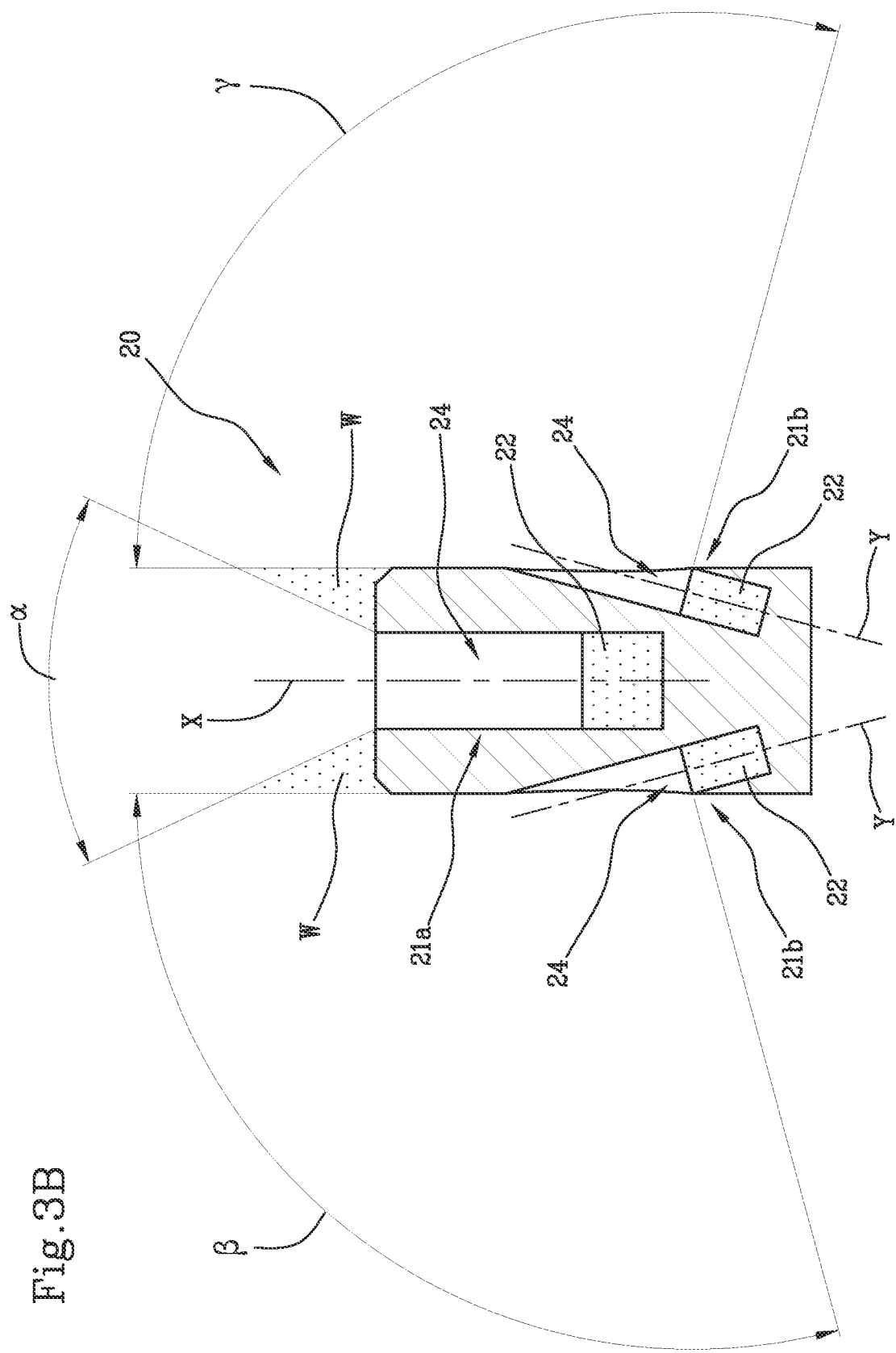

As shown in FIGS. 3A and 3B, each detection element 21a, 21b comprises at least one scintillation crystal 22 and a corresponding first electronic conversion electronics (not illustrated) for receiving an optical signal from the scintillation crystal 22 and converting it into an electric signal. Preferably, the scintillation crystals 22 are sensitive to gamma rays of strength between 30 keV and 1 MeV, which emit light at peak wavelength as a function of their composition in a range from 300 nm-600 nm.

With reference to the embodiment shown in the accompanying drawings, each detection element 21a, 21b is also associated with a respective collimator 24.

Preferably, each collimator 24 is made in the form of a blind channel, made in the material of the detection head 20, on the bottom of which the respective scintillation crystal 22 lies in such a way that a portion of the lateral wall of the channel, included between the crystal 22 and the outer opening of the channel, defines a solid detection angle a, b, and therefore determines the collimation of the radiation directed towards the crystal 22.

Still more preferably, each collimator 24 is made of a material with a high atomic number and is therefore suitable for blocking the gamma rays incident upon the detection element 21a, 21b with an external solid angle a, b, defined by the respective collimator 24. In this way, only gamma radiation having an angle inside the solid detection angle a, b, can be actually absorbed by the scintillation crystal 22 and converted, by the first electronic converter circuitry, into an electrical signal.

According to variant embodiments, the collimators 24 can be made in the form of inserts applied to a load-bearing structure defining the detection head 20.

The amplitudes of the solid detection angles a, b may vary depending on the positioning of the scintillation crystal 22 inside the collimator 24. More specifically, the opening of the solid detecting angles a, b decreases the more the scintillation crystal 22 is inserted deep in the collimator 24.

In the preferred embodiment, the scintillation crystal 22 of the central detection element 21a is inserted in the respective collimator 24 at a position behind the outlet point of the collimator 24, while the lateral detection elements 21b are inserted close to an outlet point of the respective collimators 24.

As shown in FIGS. 3A and 3B, the solid angle a relative to the central detection element 21a has a greater or lesser amplitude (measured in the plane of symmetry "I") depending on how much the scintillation crystal 22 is inserted in the collimator 24. In FIG. 3B, the scintillation crystal 22 is inserted further in depth than the scintillation crystal 22 shown in FIG. 3A and therefore the solid detection angle a associated with it has a smaller opening than that shown in FIG. 3A. Consequently, the radiation is more focused, that is to say, the spatial resolution associated with the central detection element 21a is greater than that associated with the central detection element 21a shown in FIG. 3A.

The scintillation crystals 22 associated with the lateral detection elements 21b are, on the other hand, inserted in the respective collimators 24 in such a way as to be preferably flush with an outer lateral surface of the detection head 20.

In other words, the scintillation crystals 22 associated with the lateral detection elements 21b have a flush edge of the outer surface of the detection head 20 and have a flat front surface inclined forwards from the edge. In this configuration, thanks to the flush wall arrangement of the scintillation crystals 22, the solid angle b, described by them starts from a generatrix of the outer wall as shown in FIGS. 3A and 3B. In this way, the detection elements 21a, 21b define respective solid detection angles a, b, g which do not overlap at least within a distance of between 1 and 7 cm from a front surface of the detection head 20.

Advantageously, the above-mentioned arrangement of the scintillation crystals 22 inserted in the collimators 24 makes it possible to increase the precision and reliability of the detector "R" reducing the blind detection zones "W", that is to say, those zones not included in any solid detection angle a, b, g.

Advantageously, this arrangement of the detection elements 21a, 21b makes it possible to increase the size of the investigation zone while maintaining the miniaturized dimensions of the detection head 20.

Advantageously, this arrangement of the scintillation crystals 22 makes it possible to obtain a detector "R" which is able to speed up the localization of the part of the patient affected by the tumor or disease since the lateral detection elements 21b form a solid detecting angle b, g which is large and suitable to act as a "directionality sensor" for the directing of the detector "R", whilst the central detection element 21a defines a solid detection angle a designed to act as an actual detector. In other words, the lateral detection elements 21b, defining a larger solid detecting angle b, probe a large area of analysis with a smaller spatial resolution so as to indicate from where the majority of gamma radiation comes. The central detection element 21a, on the other hand, defining a smaller solid detecting angle a, has a better spatial resolution and is therefore directed on the basis of the information deriving from the lateral detection elements 21b in such a way as to perform the actual detection operation.

In order to further increase the precision and speed of identifying the zone affected by tumor cells (or by specific pathologies), the central detection element 21a has a larger volume than each of the lateral detection elements 21b and an angular opening which is less than each of the lateral detection elements 21b, as mentioned above. Preferably, the solid detection angle a, defined by the central detection element 21a has an amplitude, measured in the plane of symmetry "I" of the detection head 20, of between 30° and 65°.

Preferably, the solid detection angle b, defined by the lateral detection elements 21b, has an amplitude, measured in the above-mentioned plane of symmetry "I", greater than 90°.

Thanks to these geometrical and structural characteristics, the central detection element 21a has a greater focusing of the gamma radiation and therefore a greater spatial resolution, whilst the lateral detection elements 21b act as directionality sensors of the detector "R" since they have a low spatial resolution but a large detection angle and therefore a wide field of analysis.

In other words, the opening of the solid angle a of the central detection element 21a allows the latter to focus more closely the incident gamma radiation increasing the resolution of the detector "R" whilst the opening of the solid angle b, g described by the lateral detection elements 21b also allows the lateral zones to be scanned relative to that covered by the central detection element 21a in such a way as to allow immediate identification of the high radiation emission zones and hence affected by tumorous diseases.

Advantageously, the volumetric size of the detection elements 21a, 21b and their position makes it possible to extend the entire investigation zone, that is to say, increasing the solid detecting angles a, b, g but at the same time allows miniaturized dimensions of the entire detection probe "S" to be maintained. This is particularly advantageous in the case of laparoscopic probes "S3", "S4", that is to say, probes which must be inserted in trocars.

Advantageously, the ratio between the dimensions of the detection elements 21a, 21b and the respective solid detecting angles a, b makes it possible to perform a reliable and precise analysis. In particular, the detection probe "S" has a geometry allowing only one or a maximum of two detection elements 21a, 21b on three to be involved simultaneously in a scintigraphy detection operation in such a way that it can be clearly understood towards which direction it is necessary to orient the detector "R" to identify the positioning of tumor. In fact, the third detection element 21b, especially in the presence of a single source of gamma radiation, that is to say, in the presence of a single tumor, only registers background events which have no contribution in locating the tumor and do not therefor influence the effectiveness of the analysis.

According to alternative embodiments, not illustrated, the scintillation crystals 22 associated with the lateral detection elements 21b are positioned further behind the above-mentioned flush position, however preferably defining respective solid detecting angles b, g which are greater than the solid detecting angle a of the scintillation crystal 22 associated with the central detection element 21a.

The orientation of the detection probe "S", and hence the detection head 20, during the medical analysis is performed manually by an operator who directs the detection probe "S" by means of the handgrip "I". The handgrip "I" has a transversal dimension greater than the transversal dimension of the supporting rod 10 and it is equipped internally with a second electronics circuitry for converting the signals (not illustrated) configured for converting the analogue signals deriving from the first electronic converter circuitry into digital signals and, if necessary, for performing a first processing of these signals.

As shown in FIGS. 1A and 1B, the handgrip "I" is reversibly connectable to the detection probe "S", and in particular to a second end 10b of the supporting rod 10, by means of a mechanical connector 12 equipped with electrical contacts in such a way that the signals, coming from the first electronic conversion electronics of the scintillation crystals 22, are transferred to the second electronic conversion electronics.

Preferably, the mechanical connector 12 is positioned at a variation of transversal cross-section between the handgrip "I" and the supporting rod 10 in such a way that the second end 10b of the supporting rod 10 can be inserted inside the handgrip "I" and locked by the interaction of the mechanical connector 12 with the handgrip "I".

In the preferred embodiment illustrated in the accompanying drawings, the mechanical connector 12 is made in the form of a bayonet coupling.

According to different embodiments, the mechanical connector 12 may be made in the form of a quick coupling, a Snap-On coupling, a threaded connection or a threaded ring nut.

Advantageously, thanks to the mechanical connector 12 it is possible to connect a plurality of different detection probes "S" to the handgrip "I" in a quick and easy manner.

Moreover, the possibility of connecting and removing the handgrip "I" from the supporting rod 10 considerably reduces the costs relative to the entire detector "R" since it is not necessary to have a handgrip "I" for each detection probe "S" but it is sufficient to have a single handgrip "I" connectable to several detection probes "S" having the mechanical connector 12.

According to another aspect of the invention, in accordance with the embodiment of FIG. 2, the detection head 20 may also be associated with the first end 10a of the supporting rod 10 by means of a mechanical connector 12 equipped with electrical contacts for transferring the signal from the first conversion electronics to at least one electrical conductor inside the supporting rod 10.

In other words, the detection head 20 can be reversibly coupled to the first end 10a of the supporting rod 10 in such a way that several different detection heads 20 can be applied to the end 10a of a same supporting rod 10. This aspect is particularly advantageous in the case of laparoscopic probes "S4" which may have telescopic extensions at the second end 10b of the supporting rod 10, which are elongated or retracted according to the medical requirements or to replace the supporting rod 10 with another of different length.

Preferably, as described above, the mechanical connector 12 reversibly connecting the detection head 20 to the supporting rod 10 is identical to the mechanical connector 12 defining the connection between the supporting rod 10 and the handgrip "I".

The detector "R" also comprises a control unit 30 connected to the second conversion electronics and capable of controlling the detection elements 21a, 21b independently so that some of them can be switched on while the others are switched off.

In other words, by means of the control unit 30, the individual detection elements 21a, 21b can be used individually independently so as to have the possibility of working with solid detecting angles a, b, g according to the requirements.

Preferably, the control unit 30 is connected to the second electronic conversion circuitry of the handgrip "I" by Wi-Fi, Bluetooth or via cable in such a way that the signals are transmitted from the second electronic converter to the control unit 30.

As shown in FIG. 1B, the control unit 30 comprises a monitor, which shows to the operator the processing of the signals coming from the detector "R" and the count parameters recorded, in particular by providing a graphical image representing in a graphical and easily legible manner the data contained in these signals.

Preferably, the control unit 30 also comprises, integrated thereto, a sound signaling device (not illustrated) configured to emit an acoustic signal which is directional or at a different intensity/frequency according to the detection element 21a, 21b most affected by the radiation at a given instant.

Alternatively, or in addition to the sound signaling device, the control unit 30 also comprises a visual signaling device, for example a flashing LED, configured to emit a visual signal according to the detection element 21a, 21b struck most by the radiation at a given instant.

The control unit 30, following processing of the signals from the detector "R", thus informs the operator about the direction of greatest origin of the gamma radiation and hence about the direction in which the detector "R" and, more specifically, the central detection element 21a, should be positioned.

The use of the monitor together with acoustic and/or visual signals thus constitutes a "navigation system" inside a cavity of the patient since the operator can easily direct the detector "R" in the direction of greatest flow of gamma radiation thus tracing the part of the patient affected by the presence of the disease.

Advantageously, using the control unit 30, locating the area affected by the presence of tumor cells or other specific diseases is simple, precise and fast.

In use, therefore, gamma radiation having different directions strikes the detection head 20 but only the radiations having directions inside the solid angles a, b, g, defined by the detection elements 21a, 21b are effectively absorbed and converted into electrical signals by the first conversion electronics. These electrical signals are transmitted to the second electronic conversion circuitry contained in the handgrip "I" in such a way as to be transformed into digital signals. Subsequently, the signals are sent to the control unit 30 which analyses them, processes and displays them on a monitor in such a way as to provide a directing of the detector "R". Since the position of the detection elements 21a, 21b are correlated with each other, it is therefore possible, given the measured intensity of radiation, to provide the direction in which to direct the detector "R" by means of the handgrip "I".

If most of the activity is detected by a transversal detection element 21b, on the right or left relative to the axial direction, then the signal to orient the detector "R" is provided by the luminous or audio signaling device of the control unit 30 which indicates the direction in which to orient the central detection element 21a.

According to another aspect of the invention, the directional gamma detector "R", as described above, can be assembled starting from a kit "K" designed to allow a plurality of different configurations.

As shown in FIG. 4, the kit "K" comprises a single handgrip "I" and a plurality of detection probes "S", each selectively connectable to the handgrip "I" using the mechanical connector 12. In detail, the plurality of detection probes "S" comprises at least one longitudinal probe "S2" (that is to say, a probe with a main collimator coaxial with the longitudinal axis of extension of the probe), an angular probe "S1" (that is to say, a probe with a main collimator which is inclined at an acute angle to the longitudinal axis of extension of the probe) and a laparoscopic probe "S3", "S4". Each of these probes may be provided at the second end 10b of the supporting rod 10 of the mechanical connector 12 or be integrated with the respective detection head 20.

Preferably, at least the laparoscopic probe "S4" has the detection head 20 removably connected or connectable to the respective supporting rod 10 by means of the further mechanical connector 12. Advantageously, the mechanical connector 12 of the handgrip "I" acts as a "universal connection" in such a way that a plurality of different supporting rods 10 can be associated with a single handgrip "I". Similarly, the further mechanical connector 12 allows a single detection head 20 to be used with two or more different supporting rods 10 (for longitudinal, angular or laparoscopic probes, respectively).

The invention achieves the preset aims eliminating the drawbacks of the prior art.

In effect, the structure of the detector "R" according to the invention allows an investigation on a three-dimensional zone encompassing, in a longitudinal plane of the detector "R", a very large angle.

Moreover, the structure of the detection elements 21a, 21b inserted at different depths in the collimators 24 makes it possible to achieve optimum collimation of the radiation with an increase in the overall resolution, in particular defining a large detection angle at the sides and a high spatial resolution in the front zone.

Moreover, the possibility of connecting/removing the handgrip "I" from the detection probe "S" makes it possible to reduce the costs relative to the detector "R" and to increase its versatility.

Furthermore, the arrangement and size of the detection elements 21a, 21b means that the procedure for determining parts of the patient affected by tumor cells or specific disease cells is simplified, speeded up and more precise. In effect, the greater dimension (volume) or surface extension of the central crystal makes it possible to optimize the space inside the detection head, giving more space to the central crystal designed for high precision detection of the radiation source, with the lateral crystals only performing a single "directional" function without specific precision requirements. Lastly, the detector "R" according to the invention is compact and thus very easy to handle and suitable for intraoperative investigation inside the patient's body cavities.

The invention claimed is:

1. A directional gamma detector comprising a detection probe and a handgrip, wherein said detection probe comprises:
    a supporting rod;
    a detection head coupled or integrated with a first end of said supporting rod and comprising a plurality of detection elements which are separate from each other for simultaneously detecting gamma radiation directed along respective directions different to each other, each detection element comprising at least one scintillation crystal and a corresponding first electronic conversion circuitry for receiving an optical signal from the crystal and converting the optical signal from the crystal into an electrical signal, each of said detection elements being associated with a respective collimator made of a material with a high atomic number and suitable to screen the gamma radiation striking said detection element with a predetermined external angle and a solid angle;
and wherein said handgrip can be gripped manually by an operator and is equipped internally with a second electronic circuitry for converting and/or processing the signals;
wherein said measuring probe is reversibly connectable to the handgrip by means of a mechanical connector equipped with electrical contacts for transferring the signals from said first electronic conversion circuitry to said second electronic circuitry for converting and/or processing the signals;
    wherein said plurality of detection elements comprises a central detection element, aligned with a main collimation axis, and at least one pair of lateral detection elements aligned along respective collimation directions transversal to said main axis of collimation.

2. The detector according to claim 1, wherein the detection head is removably coupled with the first end of said supporting rod by means of a mechanical connector equipped with electrical contacts for transferring the signals from said first electronic conversion circuitry to at least one electrical conductor inside the supporting rod.

3. The detector according to claim 2, wherein said mechanical connector is of the type selected between: bayonet coupling; quick coupling; snap-on coupling, threaded connection or threaded ring nut.

4. The detector according to claim 2, wherein said handgrip has a transversal dimension which is greater than said supporting rod and wherein said mechanical connector is positioned at a variation in the transversal cross section between the handgrip and the supporting rod.

5. The detector according to claim 1, wherein said mechanical connector is of the type selected between: bayonet coupling; quick coupling; snap-on coupling, threaded connection or threaded ring nut.

6. The detector according to claim 5, wherein said handgrip has a transversal dimension which is greater than said supporting rod and wherein said mechanical connector is positioned at a variation in the transversal cross section between the handgrip and the supporting rod.

7. The detector according to claim 1, wherein said handgrip has a transversal dimension which is greater than said supporting rod and wherein said mechanical connector is positioned at a variation in the transversal cross section between the handgrip and the supporting rod.

8. The detector according to claim 1, wherein said lateral detection elements have the respective scintillation crystal positioned flush with an outer lateral surface of said detection head.

9. The detector according to claim 1, wherein said detection elements define respective solid detection angles which do not overlap at least within a distance of between 1 and 7 cm from a front surface of the detection head.

10. The detector according to claim 5, wherein said central detection element has a volume greater than each of said lateral detection elements and an angular opening lower than each of said lateral detection elements.

11. The detector according to claim 10, wherein the solid detection angle defined by said central detection element has an amplitude, measured on a plane of symmetry of the detection head passing through the central collimation axis, of between 30° and 65° and wherein the solid detection angle defined by said lateral detection element has an amplitude greater than 90°, measured on said plane of symmetry.

12. The detector according to claim 1, wherein the lateral detection elements are positioned symmetrically about a longitudinal plane passing through said main collimation axis.

13. The detector according to claim 1, wherein said plurality of detection elements comprises a plurality of lateral detection elements aligned along respective collimation directions transversal to the main collimation axis and angularly positioned at predetermined angular distances around the central detection element.

14. The detector according to claim 1, wherein the lateral detection elements are shaped and/or positioned in such a way that at least a part of the central detection element is located in a region of the detection head radially located between said lateral detection elements and/or between respective channels in which the lateral detection elements are located.

15. A scintigraphic detection kit which can be assembled according to a plurality of different configurations and configured for making a directional gamma detector according to claim 1, comprising:
    a single handgrip;
    a plurality of detection probes, each selectively connectable to said handgrip by means of said mechanical connector;
wherein said plurality of detection probes comprises at least one longitudinal probe, an angular probe and a laparoscopic probe.

16. The kit according to claim 15, wherein at least one of said probes comprises a supporting rod and a detection head removably connected or connectable to the supporting rod by means of a further mechanical connector.

17. The kit of claim 16, wherein the kit comprises a single detection head and each of said detection probes comprises a respective supporting rod on which said detection head is removably connectable.

18. The detector of claim 1, wherein the second end of the supporting rod is reversibly connectable to the handgrip.

19. The detector of claim 1, wherein the central detection element, aligned with a main collimation axis is parallel to a main direction of extension of the supporting rod, and wherein the at least one pair of lateral detection elements are divergent away from the handgrip.

* * * * *